(12) United States Patent
Oshimura et al.

(10) Patent No.: US 8,802,065 B2
(45) Date of Patent: Aug. 12, 2014

(54) AQUEOUS PRESERVATIVE SOLUTION WITH HIGH AMINO ACID CONTENT

(75) Inventors: Eiko Oshimura, Kawasaki (JP); Kazuhiko Tobita, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 526 days.

(21) Appl. No.: 12/101,467

(22) Filed: Apr. 11, 2008

(65) Prior Publication Data

US 2008/0260672 A1    Oct. 23, 2008

(30) Foreign Application Priority Data

Apr. 13, 2007  (JP) ................ 2007-106161

(51) Int. Cl.
*A61K 8/44* (2006.01)
*C09K 15/04* (2006.01)
*A61Q 5/00* (2006.01)

(52) U.S. Cl.
USPC ......................................... 424/70.1; 252/399

(58) Field of Classification Search
None
See application file for complete search history.

(56) References Cited

U.S. PATENT DOCUMENTS

| 4,590,069 | A |  | 5/1986 | Deckner et al. |
| 4,981,845 | A | * | 1/1991 | Pereira ............................ 514/657 |
| 5,352,695 | A | * | 10/1994 | N'Guyen et al. ............... 514/423 |
| 5,785,962 | A |  | 7/1998 | Hinz et al. |
| 6,197,317 | B1 | * | 3/2001 | Klein ............................. 424/401 |
| 6,821,780 | B2 |  | 11/2004 | Thorel et al. |

FOREIGN PATENT DOCUMENTS

| GB | 2 321 595 | 8/1998 |
| JP | 2005-128220 | 5/2005 |
| JP | 2006-290787 | 10/2006 |
| KR | 1020090054777 | 6/2009 |

OTHER PUBLICATIONS

Michalun, Skin care and Cosmetic Ingredient Dictionary, Milady Publishing, 1994.*
Japanese Office Action issued Jan. 11, 2012, in Japanese Patent Application No. 2007-106161 (with English Translation).
Koshohin Iyakuhin Bofu Sakkinzai no Kagaku, Fragrance Journal Ltd., (1990).
Bokin Bobai Handbook p. 3, Gihodo Shuppan Co., Ltd., (1986).
Antimicrobial Effects of Lactates: A Review, Journal of Food Protection, vol. 57, No. 5, Abstract (1994).

\* cited by examiner

*Primary Examiner* — Dennis Heyer
(74) *Attorney, Agent, or Firm* — Oblon, Spivak, McClelland, Maier & Neustadt, L.L.P.

(57) ABSTRACT

Aqueous preservative solutions with a high amino acid content which is excellent in preservation, particularly a preservative effect on fungi, and safety, and is excellent in storage stability so as not to cause a problem such as depositing, coloring or smelling even when it is stored for a long time, and when incorporated in a cosmetic, is capable of imparting a high moisturizing effect without causing a sticky feeling, and imparting an effect of preventing dyed hair from color fading, can be achieved by incorporating pyrrolidone carboxylic acid and/or a salt thereof (Component A), a basic amino acid and/or a salt thereof (Component B), an acidic amino acid and/or a salt thereof (Component C), a neutral amino acid and/or a salt thereof (Component D) and lactic acid and/or a salt thereof (Component E) at a specific incorporation ratio and at a specific pH.

28 Claims, No Drawings

AQUEOUS PRESERVATIVE SOLUTION WITH HIGH AMINO ACID CONTENT

CROSS REFERENCES TO RELATED APPLICATIONS

This application claims priority to Japanese Patent Application No. 106161/2007, filed on Apr. 13, 2007, which is incorporated herein by reference in its entirety.

BACKGROUND OF THE INVENTION

1. Field of the Invention

The present invention relates to aqueous preservative solutions with a high amino acid content and cosmetics which contain such a preservative solution.

2. Discussion of the Background

Amino acids or derivatives thereof are useful materials that can be widely used in various cosmetics such as skin cosmetics and hair cosmetics. Due to an increase in the desire for cosmetics made of natural materials in recent years, several kinds of amino acids or derivatives thereof have come to be frequently incorporated therein. However, their quality control or incorporating operation has been extremely complicated. Therefore, an aqueous solution in which versatile and useful amino acids or derivatives thereof are dissolved at a high concentration in advance has been desired. However, in general, such an aqueous solution containing amino acids at a high concentration is easily degraded and deposition is easily caused depending on the amino acids incorporated therein. Therefore, there has been no product which can be used in practical applications.

In general, as a preservation technique, the use of preservatives which can be incorporated in cosmetics such as p-hydroxybenzoic acid esters (parabens) and phenoxyethanol can be exemplified (see, Koshohin Iyakuhin Bofu Sakkinzai no Kagaku). However, there have been problems in that any of the preservatives have an effect only on limited species of microorganisms, respectively, and particularly they show a limited effect on fungi. Further, there have been problems that such preservatives cause irritation to the skin and the like and therefore have a tendency to have low safety, and in the case where products for sensitive skin or made of natural materials are particularly expressly stated, because such preservatives are components which do not exist in nature, an extremely negative impression is given to consumers.

A technique in which preservation is carried out by adjusting the pH of the solution to an acid pH has also been widely known (see, Bokin Bobai Handbook p. 3, Gihodo Shuppan Co., Ltd., 1986). However, when the pH of the solution is 4 or lower, at which an apparent effect is exhibited also on fungi which naturally prefer an acid pH range, the solubility of acidic amino acids is decreased to cause deposition thereof at a low temperature. Therefore, there has been a problem that dissolution stability for achieving distribution of the solution as a product cannot be obtained.

On the other hand, it has been reported that sodium lactate which is also used as a moisturizing agent has a preservative effect (see, Antimicrobial Effects of Lactates: A Review, *Journal of Food Protection*, vol. 57, no. 5, pp. 445-450 (1994)). However, it was not always effective on fungi that are resistant to osmotic pressure.

Thus, a need remains for an aqueous preservative solution with a high amino acid content which is excellent in preservation, particularly a preservative effect on fungi, and safety, and is excellent in storage stability so as not to cause a problem such as depositing, coloring or smelling even when it is stored for a long time, and by being incorporated in a cosmetic, is capable of imparting a high moisturizing effect without causing a sticky feeling, and imparting an effect of preventing dyed hair from color fading.

SUMMARY OF THE INVENTION

Accordingly, it is one object of the present invention to provide novel aqueous preservative solutions with a high amino acid content.

It is another object of the present invention to provide novel aqueous preservative solutions with a high amino acid content, which are excellent in preservation.

It is another object of the present invention to provide novel aqueous preservative solutions with a high amino acid content, which are particularly effective on fungi.

It is another object of the present invention to provide novel aqueous preservative solutions with a high amino acid content, which have a high degree of safety.

It is another object of the present invention to provide novel aqueous preservative solutions with a high amino acid content, which are excellent in storage stability.

It is another object of the present invention to provide novel aqueous preservative solutions with a high amino acid content, which exhibit a reduce tendency to deposit the amino acid from solution, even when stored for a long time.

It is another object of the present invention to provide novel aqueous preservative solutions with a high amino acid content, which do not exhibit color development, even when stored for a long time.

It is another object of the present invention to provide novel aqueous preservative solutions with a high amino acid content, which do not develop an odor, even when stored for a long time.

It is another object of the present invention to provide novel aqueous preservative solutions with a high amino acid content, which when incorporated in a cosmetic, are capable of imparting a high moisturizing effect without causing a sticky feeling, and imparting an effect of preventing dyed hair from color fading.

These and other objects, which will become apparent during the following detailed description, have been achieved by the inventors' discovery that the above object can be achieved by incorporating pyrrolidone carboxylic acid and/or a salt thereof (Component A), a basic amino acid and/or a salt thereof (Component B), an acidic amino acid and/or a salt thereof (Component C), a neutral amino acid and/or a salt thereof (Component D), lactic acid and/or a salt thereof (Component E) and water (Component F) at a specific incorporation ratio and at a specific pH, and thus the present invention was completed.

Thus, the present invention provides the following embodiments:

(1) An aqueous preservative solution with a high amino acid content, comprising:

(A) at least one pyrrolidone carboxylic acid and/or a salt thereof;

(B) at least one basic amino acid and/or a salt thereof;

(C) at least one acidic amino acid and/or a salt thereof;

(D) at least one neutral amino acid and/or a salt thereof;

(E) lactic acid and/or a salt thereof;

(F) water, wherein:

component (A) and component (E) are present in a total amount of from 25 to 40% by weight, based on the total weight of component (A), component (B), component (C), component (D), component (E), and component (F), and component (A) is present in an amount of from 5 to 95% by weight, based on the total weight of component (A) and component (E), and the pH of the solution is from 3.5 to 6.0.

(2) An aqueous preservative solution with a high amino acid content according to (1), wherein:

component (B) is arginine and/or a salt thereof, and component (B) is present in an amount of from 4 to 25% by weight, based on the total weight of component (A), component (B), component (C), component (D), and component (E).

(3) An aqueous preservative solution with a high amino acid content according to either (1) or (2), wherein:

component (C) is aspartic acid and/or a salt thereof, and component (C) is present in an amount of from 5 to 15% by weight, based on the total weight of component (A), component (B), component (C), component (D). and component (E).

(4) An aqueous preservative solution with a high amino acid content according to any one of (1) to (3), wherein:

component (D) is one kind or two or more kinds selected from glycine and/or a salt thereof and alanine and/or a salt thereof, and component (D) is present in an amount of from 5 to 20% by weight, based on the total weight of component (A), component (B), component (C), component (D), and component (E).

(5) A cosmetic comprising the aqueous preservative solution with a high amino acid content according to any one of (1) to (4).

By incorporating lactic acid and/or a salt thereof (Component E) and water (Component F) in an aqueous solution containing a high content of pyrrolidone carboxylic acid and/or a salt thereof (Component A), a basic amino acid and/or a salt thereof (Component B), an acidic amino acid and/or a salt thereof (Component C) and a neutral amino acid and/or a salt thereof (Component D) at a specific incorporation ratio and at a specific pH, it has become possible to provide an aqueous preservative solution with a high amino acid content which is excellent in preservation, particularly a preservative effect on fungi, and safety, and is excellent in storage stability so as not to cause a problem such as depositing, coloring or smelling even when it is stored for a long time, and by being incorporated in a cosmetic, is capable of imparting a high moisturizing effect without causing a sticky feeling, and imparting an effect of preventing dyed hair from color fading.

DETAILED DESCRIPTION OF THE PREFERRED EMBODIMENTS

The present invention is directed to an aqueous preservative solution with a high amino acid content, comprising pyrrolidone carboxylic acid and/or a salt thereof (Component A), a basic amino acid and/or a salt thereof (Component B), an acidic amino acid and/or a salt thereof (Component C), a neutral amino acid and/or a salt thereof (Component D), lactic acid and/or a salt thereof (Component E) and water (Component F) at a specific incorporation ratio and at a specific pH. Hereinafter, its constituting components and incorporation ratio will be described sequentially.

In the invention, the term "amino acids" means those directed to "basic amino acids or salts thereof, acidic amino acids or salts thereof, neutral amino acids and pyrrolidone carboxylic acid (PCA), which is an amino acid derivative, and/or salts thereof".

The term "a high content" means that "the ratio of the total weight of pyrrolidone carboxylic acid and/or a salt thereof (Component A), a basic amino acid and/or a salt thereof (Component B), an acidic amino acid and/or a salt thereof (Component C), and a neutral amino acid and/or a salt thereof (Component D) to the total weight of pyrrolidone carboxylic acid and/or a salt thereof (Component A), a basic amino acid and/or a salt thereof (Component B), an acidic amino acid and/or a salt thereof (Component C), a neutral amino acid and/or a salt thereof (Component D), lactic acid and/or a salt thereof (Component E) and water (Component F), which are the present constituting elements, is 15% by weight or more, preferably 18% by weight or more, more preferably 20% by weight or more, further more preferably 23% by weight or more, still further more preferably 25% by weight or more, yet still further more preferably 28% by weight or more, and particularly preferably 30% by weight or more".

Further, the term "aqueous preservative solution" does not mean "an aqueous solution which serves as a preservative such that a substance obtained by incorporating this aqueous solution exhibits a preservative effect because of the incorporation of this aqueous solution", but means "an aqueous solution having a specific preservative ability per se".

Further, the term "preservative effect" as used herein means that "a preservative effect which satisfies the evaluation criteria of preparations in Category IA (injections and other parenterals including otic and ophthalmic preparations) described in the Supplement to the Japanese Pharmacopoeia, Fourteenth Edition when a preservative effectiveness test was carried out with respect to three strains of bacteria, *Escherichia coli, Pseudomonas aeruginosa*, and *Staphylococcus aureus*, and two strains of fungi, *Candida albicans* and *Aspergillus niger* according to the method described in 15. Preservative Effectiveness Tests in the Supplement to the Japanese Pharmacopoeia, Fourteenth Edition is exhibited". That is, it means an effect that satisfies the following requirements: "the viable bacterial count is reduced to 0.1% or lower compared with the initial inoculum count within 14 days after inoculation in the test period, and the viable bacterial count remains at the same level or decreases further for 28 days thereafter until completion of the test" and "the viable count of fungi remains at the same level or less than that of the initial inoculum count until 14 days and 28 days after inoculation". Incidentally, the constitution of this application corresponds to a preparation produced with a water-soluble base, and there is a high likelihood that it can accidentally enter the eye during handling it as a cosmetic material, therefore, the preparations in Category IA according to the Japanese Pharmacopoeia (injections and other parenterals including otic and ophthalmic preparations) are chosen.

The pyrrolidone carboxylic acid and/or a salt thereof as (Component A) to be used in the invention have/has a moisturizing effect and an effect of preventing dyed hair from color fading and acts synergistically with lactic acid or a salt thereof as (Component E) to exhibit a preservative effect in a cosmetic in which the aqueous preservative solution with a high amino acid content of the invention is incorporated. Pyrrolidone carboxylic acid in either a free form or a salt form can be used. The salt thereof is not particularly limited as long as it is a salt that can be used in a common cosmetic, and examples thereof include alkali metal salts such as sodium salts and potassium salts; alkaline earth metal salts such as calcium salts and magnesium salts; amine salts such as ammonium salts and ethanol amine salts; salts of basic amino acids such as lysine and arginine; and the like, and alkali metal salts are preferred. These may be in an optically active form (L-form or D-form) or a racemic form (DL-form). These may be used alone or by mixing two or more kinds thereof. Specific examples thereof include L-pyrrolidone carboxylic acid, sodium L-pyrrolidone carboxylate, potassium DL-pyrrolidone carboxylate, ammonium DL-pyrrolidone carboxylate and the like. From the viewpoint that dissolution stability is favorable, preferred are L-pyrrolidone carboxylic acid and alkali metal salts of L-pyrrolidone carboxylic acid, and more preferred are L-pyrrolidone carboxylic acid and a sodium salt of L-pyrrolidone carboxylic acid.

The basic amino acid and/or a salt thereof as (Component B) to be used in the invention have/has an effect of promoting the production of collagen or promoting blood circulation in the skin, and an effect of improving the prevention of dyed hair from color fading in hair. The basic amino acid is not particularly limited as long as it is a compound having amino groups more than acidic groups in its molecule, and may be either a natural compound or an unnatural compound. It does not matter whether it is used as a basic amino acid in a free form or a salt form. The salt thereof is not particularly limited as long as it is a salt that can be used in a common cosmetic, and examples thereof include inorganic acid salts such as hydrochloride salts and sulfate salts; organic acid salts such as acetate salts and citrate salts; acidic amino acid salts such as glutamic acid and aspartic acid; and the like, and hydrochloride salts are preferred (with the proviso that in the case of using an acidic amino acid salt, it is considered as a combination of amino acids in a free form, and a basic amino acid moiety is classified into (Component B) and an acidic amino acid moiety is classified into (Component C)). These may be in an optically active form (L-form or D-form) or a racemic form (DL-form), however, L-form is preferred. These may be used alone or by mixing two or more kinds thereof. Specific examples thereof include L-lysine, D-lysine, DL-lysine, L-lysine hydrochloride, L-lysine sulfate, L-lysine acetate, L-hydroxylysine, D-hydroxylysine, DL-hydroxylysine, L-hydroxylysine hydrochloride, L-hydroxylysine sulfate, L-hydroxylysine acetate, L-arginine, D-arginine, DL-arginine, L-arginine hydrochloride, L-arginine sulfate, L-arginine acetate, L-histidine, D-histidine, DL-histidine, L-histidine hydrochloride, L-histidine sulfate, L-histidine acetate, L-ornithine, D-ornithine, DL-ornithine, L-ornithine hydrochloride, L-ornithine sulfate, L-ornithine acetate, and the like. From the viewpoint that the affinity for the skin or hair is high and a broad effect can be expected, preferred are arginine and/or salts thereof, histidine and/or salts thereof, and ornithine and/or salts thereof, more preferred are L-arginine, L-arginine hydrochloride, L-histidine, L-histidine hydrochloride, L-ornithine and L-ornithine hydrochloride, further more preferred are arginine and/or salts thereof, and particularly preferred is L-arginine or L-arginine hydrochloride.

The acidic amino acid and/or a salt thereof as (Component C) to be used in the invention have/has an effect of imparting a moisturizing effect. The acidic amino acid is not particularly limited as long as it is a compound having acidic groups such as a carboxyl group and a sulfonic acid group more than amino groups in its molecule, and may be either a natural compound or an unnatural compound. It does not matter whether it is used as an acidic amino acid in a free form or a salt form. The salt thereof is not particularly limited as long as it is a salt that can be used in a common cosmetic, and examples thereof include alkali metal salts such as sodium salts and potassium salts; alkaline earth metal salts such as calcium salts and magnesium salts; amine salts such as ammonium salts and ethanol amine salts; salts of basic amino acids such as lysine and arginine; and the like, and alkali metal salts are preferred (with the proviso that in the case of using a basic amino acid salt, it is considered as a combination of amino acids in a free form, and a basic amino acid moiety is classified into (Component B) and an acidic amino acid moiety is classified into (Component C)). These may be in an optically active form (L-form or D-form) or a racemic form (DL-form), however, L-form is preferred. These may be used alone or by mixing two or more kinds thereof. Specific examples thereof include L-aspartic acid, D-aspartic acid, DL-aspartic acid, sodium salts of L-aspartic acid, potassium salts of L-aspartic acid, magnesium salts of L-aspartic acid, L-glutamic acid, D-glutamic acid, DL-glutamic acid, sodium salts of L-glutamic acid, potassium salts of L-glutamic acid, magnesium salts of L-glutamic acid and the like. In particular, from the viewpoint that an excellent low-temperature stability can be obtained, preferred are aspartic acid and/or salts thereof, more preferred are L-aspartic acid and alkali metals salts of L-aspartic acid, and further more preferred are L-aspartic acid and sodium salts of L-aspartic acid.

The neutral amino acid and/or a salt thereof as (Component D) to be used in the invention have/has an effect of effectively reducing a sticky feeling. The neutral amino acid is not particularly limited as long as it is a compound in which the number of amino groups is identical to the number of acidic groups in its molecule, and may be either a natural compound or an unnatural compound. The salt thereof is not particularly limited as long as it is a salt that can be used in a common cosmetic, and examples thereof include alkali metal salts such as sodium salts and potassium salts; inorganic acid salts such as hydrochloric acid and sulfuric acid; and the like. These may be in an optically active form (L-form or D-form) or a racemic form (DL-form), however, L-form is preferred. These may be used alone or by mixing two or more kinds thereof. Specific examples thereof include glycine, L-alanine, D-alanine, DL-alanine, L-β-alanine, D-β-alanine, DL-β-alanine, L-taurine, D-taurine, DL-taurine, L-valine, D-valine, DL-valine, L-leucine, D-leucine, DL-leucine, L-isoleucine, D-isoleucine, DL-isoleucine, L-serine, D-serine, DL-serine, L-threonine, D-threonine, DL-threonine, L-phenylalanine, D-phenylalanine, DL-phenylalanine, L-tyrosine, D-tyrosine, DL-tyrosine, L-proline, D-proline, DL-proline, L-hydroxyproline, D-hydroxyproline, DL-hydroxyproline, L-tryptophan, D-tryptophan, DL-tryptophan, L-cysteine, D-cysteine, DL-cysteine, L-methionine, D-methionine, DL-methionine, sodium salts of glycine, potassium salts of glycine, glycine hydrochloride and the like. From the viewpoint that a sticky feeling can be prevented and a smooth feeling can be imparted without reducing a moisturizing property, preferred are glycine and/or salts thereof, and alanine and/or salts thereof, more preferred are glycine, L-alanine, D-alanine and DL-alanine, and further more preferred are glycine and L-alanine.

Lactic acid and/or a salt thereof as (Component E) to be used in the invention have/has an effect of preserving an aqueous preservative solution with a high amino acid content together with pyrrolidone carboxylic acid and/or a salt thereof as (Component A). Lactic acid and/or a salt thereof may be used as lactic acid in a free form or a salt form. The salt thereof is not particularly limited as long as it is a salt that can be used in a common cosmetic, and examples thereof include alkali metal salts such as sodium salts and potassium salts; alkaline earth metal salts such as calcium salts and magnesium salts; amine salts such as ammonium salts and ethanol amine salts; salts of basic amino acids such as lysine and arginine; and the like, and alkali metal salts are preferred. These may be in an optically active form (L-form or D-form) or a racemic form (DL-form). These may be used alone or by mixing two or more kinds thereof. Specific examples thereof include L-lactic acid, D-lactic acid, DL-lactic acid, sodium L-lactate, sodium D-lactate, sodium DL-lactate, potassium DL-lactate, ammonium DL-lactate and the like. From the viewpoint of having dissolution stability, preferred are L-lactic acid, DL-lactic acid, alkali metal salts of L-lactic acid and alkali metal salts of DL-lactic acid, and more preferred are DL-lactic acid and sodium salts of DL-lactic acid.

Water to be used as (Component F) of the invention is not particularly limited as long as it has a purity to such an extent that it is commonly used in a washing agent or a cosmetic. Specifically, ion exchanged water, well water, natural water, groundwater, tap water, hard water, soft water, or the like can be used. Among these, one kind may be used, or two or more kinds selected from the above group may be used as a mixture. From the viewpoint of the storage stability of the present inventive product or an aspect of hygiene, ion exchanged water is preferred.

The lower limit of the pH of the aqueous preservative solution with a high amino acid content of the invention is not particularly limited as long as crystal deposition of an amino acid, particularly an acidic amino acid is not caused. However, it is preferably 3.5, more preferably 4.0, further more preferably 4.3, still further more preferably 4.5, and particularly preferably 4.8. The upper limit of the pH of the aqueous preservative solution with a high amino acid content of the invention is not particularly limited as long as it has a preservative effect. However, from the viewpoint of having an effect particularly on *Aspergillus niger*, it is preferably 6.0, more preferably 5.8, further more preferably 5.6, still further more preferably 5.5, and particularly preferably 5.4.

As a technique of adjusting pH, although it is not particularly limited, the pH may be achieved either by only the incorporation amount or combination of pyrrolidone carboxylic acid as (Component A), an acidic amino acid as (Component C) and lactic acid as (Component E), all of which are acidic components of the present composition, or by additionally incorporating an organic acid such as citric acid, acetic acid, malic acid, tartaric acid or glycolic acid, or an inorganic acid such as hydrochloric acid, sulfuric acid or phosphoric acid. From the viewpoint that an excellent moisturizing effect can be obtained and also an aqueous preservative solution with a high amino acid content in which a higher content of amino acids is realized can be provided, it is preferred that the pH is achieved only by the incorporation amount or combination of pyrrolidone carboxylic acid as (Component A), an acidic amino acid as (Component C) and lactic acid as (Component E), all of which are acidic components of the present composition.

In the invention, the weight of (Component A)/[the total weight of (Component A)+(Component B)+(Component C)+ (Component D)+(Component E)] (% by weight) is preferably in the range of from 30 to 60% by weight. When an aqueous preservative solution with a high amino acid content in which the above ratio is less than 30% by weight is incorporated in a cosmetic, a sufficient moisturizing effect or a sufficient effect of preventing dyed hair from color fading cannot be obtained in some cases. When the above ratio exceeds 60% by weight, deposition of an amino acid may be caused in some cases. The lower limit of the weight of (Component A)/[the total weight of (Component A)+(Component B)+(Component C)+(Component D)+(Component E)] (% by weight) is more preferably 31% by weight, further more preferably 33% by weight, still further more preferably 35% by weight, and particularly preferably 37% by weight from the viewpoint that an aqueous preservative solution with a high amino acid content in which the content of amino acids is made as high as possible while maintaining a favorable moisturizing effect can be provided. The upper limit of the weight of (Component A)/[the total weight of (Component A)+(Component B)+ (Component C)+(Component D)+(Component E)] (% by weight) is more preferably 58% by weight, further more preferably 55% by weight, still further more preferably 53% by weight, yet still further more preferably 50% by weight, particularly preferably 48% by weight, and most preferably 45% by weight from the viewpoint that an aqueous preservative solution with a high amino acid content in which the content of amino acids is made as high as possible while maintaining a favorable moisturizing effect can be provided.

In the invention, the weight of (Component B)/[the total weight of (Component A)+(Component B)+(Component C)+ (Component D)+(Component E)] (% by weight) is preferably in the range of from 4 to 25% by weight. When an aqueous preservative solution with a high amino acid content in which the above ratio is less than 4% by weight is incorporated in a cosmetic, a sufficient effect of promoting the production of collagen or promoting blood circulation cannot be obtained in the skin, and a sufficient effect of improving the prevention of dyed hair from color fading cannot be obtained in hair in some cases. When the above ratio exceeds 25% by weight, an adverse effect on the pH adjustment may be caused to result in deviation from the pH range in some cases. The lower limit of the weight of (Component B)/[the total weight of (Component A)+(Component B)+(Component C)+(Component D)+(Component E)] (% by weight) is more preferably 6% by weight, further more preferably 8% by weight, and particularly preferably 10% by weight from the viewpoint that an aqueous preservative solution with a high amino acid content in which a high content of amino acids is achieved while providing an effect of promoting the production of collagen or promoting blood circulation in the skin, and an effect of improving the prevention of dyed hair from color fading in hair can be provided. The upper limit of the weight of (Component B)/[the total weight of (Component A)+(Component B)+(Component C)+(Component D)+(Component E)] (% by weight) is more preferably 23% by weight, further more preferably 20% by weight, still further more preferably 19% by weight, and particularly preferably 18% by weight from the viewpoint that an aqueous preservative solution with a high amino acid content in which a high content of amino acids is achieved while providing an effect of promoting the production of collagen or promoting blood circulation in the skin, and an effect of improving the prevention of dyed hair from color fading in hair can be provided.

In the invention, the weight of (Component C)/[the total weight of (Component A)+(Component B)+(Component C)+ (Component D)+(Component E)] (% by weight) is preferably in the range of from 5 to 15% by weight. When an aqueous preservative solution with a high amino acid content in which the above ratio is less than 5% by weight is incorporated in a cosmetic, an effect of imparting a moisturizing effect cannot be obtained in some cases. When the above ratio exceeds 15% by weight, deposition may be caused during storage at a low temperature in some cases. The lower limit of the weight of (Component C)/[the total weight of (Component A)+(Component B)+(Component C)+(Component D)+(Component E)] (% by weight) is more preferably 6% by weight, further more preferably 7% by weight, and particularly preferably 8% by weight from the viewpoint that a favorable moisturizing effect can be provided without causing deposition during storage at a low temperature. The upper limit of the weight of (Component C)/[the total weight of (Component A)+(Component B)+(Component C)+(Component D)+(Component E)] (% by weight) is more preferably 14% by weight, further more preferably 13% by weight, and particularly preferably 12% by weight from the viewpoint that a favorable moisturizing effect can be provided without causing deposition during storage at a low temperature.

In the invention, the weight of (Component D)/[the total weight of (Component A)+(Component B)+(Component C)+(Component D)+(Component E)] (% by weight) is preferably in the range of from 5 to 20% by weight. When an aqueous preservative solution with a high amino acid content in which the above ratio is less than 5% by weight is incorporated in a cosmetic, an effect of reducing a sticky feeling may be insufficient in some cases. When the above ratio exceeds 20% by weight, it may inhibit the other amino acids from being incorporated at a high content to cause deposition of amino acids in some cases. The lower limit of the weight of (Component D)/[the total weight of (Component A)+(Component B)+(Component C)+(Component D)+(Component E)] (% by weight) is more preferably 6% by weight, further more preferably 7% by weight, still further more preferably 8% by weight, yet still further more preferably 9% by weight, and particularly preferably 10% by weight from the viewpoint of having an effect of reducing a sticky feeling without inhibiting the other amino acids from being incorporated at a high content to cause deposition of amino acids. The upper limit of the weight of (Component D)/[the total weight of (Component A)+(Component B)+(Component C)+(Component D)+(Component E)] (% by weight) is more preferably 19% by weight, further more preferably 18% by weight, still further more preferably 17% by weight, yet still further more preferably 16% by weight, and particularly preferably 15% by weight from the viewpoint of having an effect of reducing a sticky feeling without inhibiting the other amino acids from being incorporated at a high content to cause deposition of amino acids.

In the invention, the weight of (Component E)/[the total weight of (Component A)+(Component B)+(Component C)+(Component D)+(Component E)] (% by weight) is preferably in the range of from 5 to 56% by weight. When the above ratio is less than 5% by weight, an effect of preserving the aqueous preservative solution with a high amino acid content may be insufficient in some cases. When the above ratio exceeds 56% by weight, it may inhibit the other amino acids from being incorporated at a high content to cause deposition of amino acids in some cases. The lower limit of the weight of (Component E)/[the total weight of (Component A)+(Component B)+(Component C)+(Component D)+(Component E)] (% by weight) is more preferably 8% by weight, further more preferably 10% by weight, still further more preferably 13% by weight, yet still further more preferably 15% by weight, and particularly preferably 20% by weight from the viewpoint of having a sufficient preservative effect without inhibiting the other amino acids from being incorporated at a high content to cause deposition of amino acids. The upper limit of the weight of (Component E)/[the total weight of (Component A)+(Component B)+(Component C)+(Component D)+(Component E)] (% by weight) is more preferably 50% by weight, further more preferably 45% by weight, still further more preferably 40% by weight, yet still further more preferably 35% by weight, and particularly preferably 30% by weight from the viewpoint of having a sufficient preservative effect without inhibiting the other amino acids from being incorporated at a high content to cause deposition of amino acids.

In the invention, [the total weight of (Component A)+(Component B)+(Component C)+(Component D)+(Component E)]/[the total weight of (Component A)+(Component B)+(Component C)+(Component D)+(Component E)+(Component F)] (% by weight) is preferably in the range of from 29 to 65% by weight. When the above ratio is less than 29% by weight, the respective effects and preservative abilities of the amino acids may be insufficient in some cases. When the above ratio exceeds 65% by weight, deposition of amino acids incorporated therein may be easily caused in some cases. The lower limit of [the total weight of (Component A)+(Component B)+(Component C)+(Component D)+(Component E)]/[the total weight of (Component A)+(Component B)+(Component C)+(Component D)+(Component E)+(Component F)] (% by weight) is more preferably 32% by weight, further more preferably 34% by weight, still further more preferably 36% by weight, yet still further more preferably 38% by weight, and particularly preferably 40% by weight from the viewpoint of sufficiently having the respective effects and preservative abilities of the amino acids without causing deposition of amino acids incorporated therein. The upper limit of [the total weight of (Component A)+(Component B)+(Component C)+(Component D)+(Component E)]/[the total weight of (Component A)+(Component B)+(Component C)+(Component D)+(Component E)+(Component F)] (% by weight) is more preferably 63% by weight, further more preferably 60% by weight, still further more preferably 58% by weight, yet still further more preferably 55% by weight, and particularly preferably 52% by weight from the viewpoint of sufficiently having the respective effects and preservative abilities of the amino acids without causing deposition of amino acids incorporated therein.

In the invention, [the total weight of (Component A)+(Component B)+(Component C)+(Component D)]/[the total weight of (Component A)+(Component B)+(Component C)+(Component D)+(Component E)+(Component F)] (% by weight) means % by weight of the total amino acids in the aqueous preservative solution with a high amino acid content, and is preferably in the range of from 15 to 60% by weight. When the above ratio is less than 15% by weight, the effects of the amino acids may be diluted when the amino acids are incorporated in a cosmetic in some cases. When the above ratio exceeds 60% by weight, deposition of amino acids may be accompanied in some cases. The lower limit of [the total weight of (Component A)+(Component B)+(Component C)+(Component D)]/[the total weight of (Component A)+(Component B)+(Component C)+(Component D)+(Component E)+(Component F)] (% by weight) is more preferably 18% by weight, further more preferably 20% by weight, still further more preferably 23% by weight, yet still further more preferably 28% by weight, and particularly preferably 30% by weight from the viewpoint of sufficiently having the respective effects and preservative abilities of the amino acids without causing deposition of amino acids incorporated therein. The upper limit of [the total weight of (Component A)+(Component B)+(Component C)+(Component D)]/[the total weight of (Component A)+(Component B)+(Component C)+(Component D)+(Component E)+(Component F)] (% by weight) is more preferably 58% by weight, further more preferably 55% by weight, still further more preferably 53% by weight, yet still further more preferably 50% by weight, and particularly preferably 45% by weight from the viewpoint of sufficiently having the respective effects and preservative abilities of the amino acids without causing deposition of amino acids incorporated therein.

In the invention, [the total weight of (Component A)+(Component E)]/[the total weight of (Component A)+(Component B)+(Component C)+(Component D)+(Component E)+(Component F)] (% by weight) is used in the range of from 25 to 40% by weight. When the above ratio is less than 25% by weight, the specific gravity of the aqueous preservative solution with a high amino acid content is lowered and a preservative effect may be insufficient in some cases. When the above ratio exceeds 40% by weight, it may adversely affect the solubility of amino acids to cause deposition of amino acids in some cases. The lower limit of [the total weight of (Component A)+(Component E)]/[the total weight of (Component A)+(Component B)+(Component C)+(Component D)+(Component E)+(Component F)] (% by weight) is more preferably 26% by weight, further more preferably 27% by weight, still further more preferably 28% by weight, yet still further more preferably 29% by weight, and particularly preferably 30% by weight from the viewpoint that an aqueous preservative solution with a high amino acid content in which the content of amino acids is made as high as possible while maintaining a favorable preservative effect can be provided. The upper limit of [the total weight of (Component A)+(Component E)]/[the total weight of (Component A)+(Component B)+(Component C)+(Component D)+(Component E)+(Component F)] (% by weight) is more preferably 39% by weight, further more preferably 38% by weight, still further more preferably 37% by weight, yet still further more preferably 36% by weight, and particularly preferably 35% by weight from the viewpoint that an aqueous preservative solution with a high amino acid content in which the content of amino acids is made as high as possible while maintaining a favorable preservative effect can be provided.

In the invention, the weight of (Component A)/[the total weight of (Component A)+(Component E)] (% by weight) is not particularly limited as long as it provides a preservative effect and does not affect deposition of amino acids and the like, and is preferably in the range of from 50 to 95% by weight. When the above ratio is less than 50% by weight, a preservative effect, particularly an effect on *Aspergillus niger* may be insufficient in some cases. Further, also when the above ratio exceeds 95% by weight, a preservative effect, particularly an effect on *Aspergillus niger* may be similarly insufficient in some cases. The lower limit of the weight of (Component A)/[the total weight of (Component A)+(Component E)] (% by weight) is more preferably 52% by weight, further more preferably 54% by weight, still further more preferably 56% by weight, and particularly preferably 60% by weight from the viewpoint that an effect particularly on *Aspergillus niger* is effective. The upper limit of the weight of (Component A)/[the total weight of (Component A)+(Component E)] (% by weight) is more preferably 90% by weight, further more preferably 85% by weight, still further more preferably 80% by weight, yet still further more preferably 75% by weight, and particularly preferably 70% by weight from the viewpoint that an effect particularly on *Aspergillus niger* is effective.

To the aqueous preservative solution with a high amino acid content of the invention, a variety of additives that are used in common cosmetics can be added to such an extent that the effect of the invention is not impaired. Such an additive can be appropriately selected by a person skilled in the art according to a desired characteristic, and the type thereof is not particularly limited. However, a water-soluble compound that does not impair the property as a transparent aqueous solution is preferred. Further, in order to maximally utilize the effect as a cosmetic material, the total incorporation amount of the additives is preferably 5% or less based on the total weight of the aqueous preservative solution with a high amino acid content. Examples of the additives include organic salts, hydrolyzed proteins, alcohols, extracts, water-soluble vitamins, enzymes, antiinflammatory agents, antioxidants, chelating agents, dyes, wetting agents, moisturizing agents, surfactants, water-soluble polymers and the like.

The aqueous preservative solution with a high amino acid content of the invention can be diluted with water and used as a cosmetic, and also can be incorporated in a cosmetic as a part of constituting elements to prepare a cosmetic. For example, cosmetics for washing such as face soaps, face washes (in the form of a cream, a paste, a liquid and a gel, using an aerosol and the like) and shampoos, hair cosmetics such as hair treatments (hair treatments in the form of a cream, a mist, a gel or in the other form, and including coating preparations for split ends) and hair setting preparations (setting lotions, curler lotions, hair pomades, stick pomades for cosmetic purposes, hair sprays, hair mists, hair liquids, hair foams, hair gels and watery greases), basic skin care cosmetics such as general creams, milky lotions (cleansing creams, cold creams, vanishing creams, hand creams and the like), creams for shaving (after-shaving creams, shaving creams and the like), skin lotions (hand lotions, general skin lotions and the like), lotions for shaving (after-shaving lotions, shaving lotions and the like), skin care oils and facial masks, cosmetics for makeup such as foundations (in the form of a cream, a liquid, and the like), eye creams and eye shadows mascaras, perfumes such as general perfumes, perfumed pastes and perfumed powders, suntan and sunscreen cosmetics such as suntan and sunscreen creams, suntan and sunscreen lotions, nail cosmetics such as nail creams, nail enamels and nail enamel removers, eyeliner cosmetics, lip cosmetics such as lipsticks and lip creams, oral cosmetics such as toothpastes, bath cosmetics such as bath salts, and the like can be exemplified. From the viewpoint that a moisturizing effect of a salt of pyrrolidone carboxylic acid and amino acids and an effect of preventing dyed hair from color fading are particularly expected, preferred are cosmetics for washing, hair cosmetics, and basic skin care cosmetics, more preferred are hair cosmetics, and further more preferred are hair treatments (hair treatments in the form of a cream, a mist, an oil, a gel or in the other form, and including coating preparations for split ends) and hair setting preparations (setting lotions, curler lotions, hair pomades, stick pomades for cosmetic purposes, hair sprays, hair mists, hair liquids, hair foams, hair gels and watery greases).

In the case where a cosmetic is prepared by incorporating the aqueous preservative solution with a high amino acid content of the invention as a part of constituting elements, it may be incorporated in an amount of about 0.01 to 20% by weight, and the incorporation amount thereof may be appropriately determined according to the type of cosmetic. From the viewpoint that the effects of the respective amino acids can be sufficiently obtained without significantly changing the hardness or viscosity of the cosmetic, the incorporation amount thereof is preferably from 0.02% by weight to 15% by weight, more preferably from 0.03% by weight to 10% by weight, and particularly preferably from 0.05% by weight to 6% by weight. In particular, in the case where it is used as a rinse-off hair cosmetic such as a hair shampoo, a hair rinse, a coloring agent or a permanent waving agent, the incorporation amount thereof is preferably from 0.1 to 6% by weight. In the case where it is used as a non rinse-off hair cosmetic such as an out bath treatment, a hair setting preparation or a brushing lotion, the incorporation amount thereof is preferably from 0.05 to 3% by weight.

Other features of the invention will become apparent in the course of the following descriptions of exemplary embodiments which are given for illustration of the invention and are not intended to be limiting thereof.

EXAMPLES

Evaluation Methods

Hereinafter, evaluation methods will be described sequentially.
Preservative Effectiveness Test.

A test was carried out according to the method described in 15. Preservative Effectiveness Tests in Supplement I to the Japanese Pharmacopoeia, Fourteenth Edition. Evaluation was carried out with reference to the evaluation criteria of preparations in Category IA (injections and other parenterals including otic and ophthalmic preparations) described in Supplement I to the Japanese Pharmacopoeia, Fourteenth Edition. That is, the evaluation criteria are as follows. The viable bacterial count is reduced to 0.1% or lower compared with the initial inoculum count within 14 days after inoculation in the test period, and the viable bacterial count remains at the same level or decreases further for 28 days thereafter until completion of the test, and the viable count of fungi remains at the same level or less than that of the initial inoculum count until 14 days and 28 days after inoculation. The case where the evaluation criteria of preparations in Category IA described in Supplement I to the Japanese Pharmacopoeia, Fourteenth Edition are satisfied was evaluated as ○, the case where the evaluation criteria are not satisfied was evaluated as X, and the case where the result exceeds the evaluation criteria of preparations in Category IA described in Supplement I to the Japanese Pharmacopoeia, Fourteenth Edition was evaluated as ○○. The case where the result exceeds the evaluation criteria of preparations in Category IA described in Supplement I to the Japanese Pharmacopoeia, Fourteenth Edition refers to a case where in the case of bacteria, the viable bacterial count is reduced to 0.1% or lower compared with the initial inoculum count within 7 days after inoculation in the test period, and the viable bacterial count remains at the same level or decreases further for 28 days thereafter until completion of the test, and in the case of fungi, the viable count of fungi is reduced to 10% or lower compared with the initial inoculum count within 28 days after inoculation.

Low-Temperature Stability.

A transparent glass bottle with a capacity of 50 mL was filled with an aqueous preservative solution with a high amino acid content, and closed with a cap and then left stand at −5° C. After one month, the dissolution state of a mixture immediately after the bottle was taken out from a storage chamber was visually evaluated based on the following evaluation criteria.

○○: Deposition, separation or freezing is not observed after storage at −5° C. for one month and the dissolution state is not changed.

○: Any of deposition, separation and freezing is observed after storage at −5° C. for one month, however, by leaving the bottle at 25° C. for one hour, it becomes a clear and colorless uniform solution.

Δ: Any of deposition, separation and freezing is observed after storage at −5° C. for one month, however, by stirring the mixture at 25° C. for one hour, it becomes a clear and colorless uniform solution.

X: Any of deposition, separation and freezing is observed after storage at −5° C. for one month, and even by stirring the mixture at 25° C. for one hour or more, it does not become a uniform solution.

Moisturizing Effect.

Two types of hair liquid formulations with a composition shown in the following Table 1 were prepared. Each of the hair liquid formulations in an amount of 0.5 mL was applied to a hair bundle with a length of about 20 cm and a weight of about 3 g and dried with a dryer while spreading it with a comb. A sensory evaluation was carried out by 5 panelists in terms of a moist feeling after one hour and ranked based on the following criteria. Then, the case where an average point is 3.1 or higher was evaluated as ○○, the case where an average point is from 2.5 to 3.0 was evaluated as ○, the case where an average point is from 2.0 to 2.4 was evaluated as Δ, and the case where an average point is 1.9 or lower was evaluated as X.

4: Test formulation gives a moist feeling much more than Comparative formulation.
3: Test formulation gives a moist feeling a little more than Comparative formulation.
2: Test formulation gives a moist feeling to the same extent as Comparative formulation.
1: Comparative formulation gives a moist feeling a little more than Test formulation.
0: Comparative formulation gives a moist feeling much more than Test formulation.

Stickiness.

Two types of hair liquid formulations shown in the following Table 1 were prepared. Each of the hair liquid formulations in an amount of 0.5 mL was applied to a hair bundle with a length of about 20 cm and a weight of about 3 g and dried with a dryer while spreading it with a comb. A sensory evaluation was carried out by 5 panelists in terms of a sticky feeling of Test formulation compared with Comparative formulation after one hour and ranked based on the following criteria. Then, the case where an average point is 3.1 or higher was evaluated as ○○, the case where an average point is from 2.5 to 3.0 was evaluated as ○, the case where an average point is from 2.0 to 2.4 was evaluated as Δ, and the case where an average point is 1.9 or lower was evaluated as X.

4: Test formulation gives a much less sticky feeling than Comparative formulation.
3: Test formulation gives a little less sticky feeling than Comparative formulation.
2: Test formulation gives a sticky feeling to the same extent as Comparative formulation.
1: Comparative formulation gives a little less sticky feeling than Test formulation.
0: Comparative formulation gives a much less sticky feeling than Test formulation.

TABLE 1

(Amounts in % by weight)

| | | Test formulation | Comparative formulation |
|---|---|---|---|
| Aqueous preservative solution with a high amino acid content (test liquid) | | 1.5 | 0.0 |
| Base formulation | POE (25) glyceryl monopyroglutamate | 1.2 | 1.2 |
| | POE (40) hydrogenated castor oil monopyroglutamate | 0.3 | 0.3 |
| | Octyldodecanol | 0.1 | 0.1 |
| | Butylene glycol | 5.0 | 5.0 |
| | Methylparaben | 0.1 | 0.1 |
| | Ethanol | 10.0 | 10.0 |
| | Carboxymethyl cellulose | 0.6 | 0.6 |
| | Water | Balance | Balance |
| Total | | 100.0 | 100.0 |

Prevention of Dyed Hair from Color Fading.

A hair bundle of highly bleached hair (light brown) with a length of about 10 cm and a weight of about 1 g was dyed with a commercially available oxidative hair dye (red) according to the instruction for use. The dyed hair bundle was immersed in 50 mL of a liquid obtained by diluting an aqueous preservative solution with a high amino acid content to 20-fold for 30 minutes and rinsed with tap water. After drying, the hair bundle was washed three times with a commercially available hair shampoo, and then, the color thereafter was evaluated according to the following criteria. Hair bundles were separately prepared by immersing the dyed hair bundles in ion exchanged water for 30 minutes, and 4 reference controls were prepared as follows: Control 0: without shampooing; Control 1: with shampooing using a commercially available hair shampoo once; Control 2: with shampooing using a commercially available hair shampoo twice; and Control 3: with shampooing using a commercially available hair shampoo three times.

○○: The color is the same as that of Control 0.
○: The color is the same as that of Control 1.
Δ: The color is the same as that of Control 2.
X: The color is the same as that of Control 3.

Examples 1 to 9 and Comparative Examples 1 to 8

Aqueous preservative solutions with a high amino acid content (Examples 1 to 9 and Comparative Examples 1 to 8) with a composition shown in the following Table 2 were prepared, and tests were carried out in terms of a preservative effect, low-temperature stability, a moisturizing property, stickiness, and color fading. Incidentally, the amount of each incorporated component shown in the table (a numerical value in the table) is represented by a weight percentage (%) when the total composition is assumed to be 100.

TABLE 2

Examples 1-9 (Amounts in % by weight).

| | | Example 1 | Example 2 | Example 3 | Example 4 | Example 5 | Example 6 | Example 7 | Example 8 | Example 9 |
|---|---|---|---|---|---|---|---|---|---|---|
| Component A | Sodium L-pyrrolidone carboxylate | 15.00 | 20.00 | 20.00 | 20.00 | 15.00 | 15.00 | | 16.75 | 15.00 |
| | Sodium DL-pyrrolidone carboxylate | | | | | | | 15.00 | | |
| | L-pyrrolidone carboxylic acid | 4.00 | | | | 4.27 | 4.27 | 4.27 | 2.78 | 4.27 |
| Component B | L-arginine | 8.00 | 8.00 | 6.00 | 8.00 | 8.00 | 8.00 | 8.00 | 8.00 | 8.00 |
| | L-lysine | | | 0.35 | | | | | | |
| | L-histidine | 0.15 | 0.15 | | 0.15 | 0.15 | 0.20 | | 0.15 | 0.20 |
| Component C | L-glutamic acid | | | | | | | | | 5.75 |
| | L-aspartic acid | 5.20 | 5.20 | 4.88 | 5.20 | 5.20 | 5.20 | 5.20 | 5.20 | |
| Component D | Glycine | 1.30 | 1.30 | 3.00 | 1.30 | 1.30 | 1.60 | 1.60 | 1.30 | 1.60 |
| | L-alanine | 1.20 | 1.20 | 2.00 | 1.20 | 1.20 | 1.50 | 3.00 | 1.20 | 1.50 |
| | L-proline | 0.40 | 0.40 | 0.10 | 0.40 | 0.40 | 0.50 | 0.50 | 0.40 | 0.50 |
| | L-serine | 0.80 | 0.80 | 1.50 | 0.80 | 0.80 | 1.00 | 1.02 | 0.80 | 1.00 |
| | L-threonine | 0.40 | 0.40 | 0.20 | 0.40 | 0.40 | 0.50 | 0.50 | 0.40 | 0.50 |
| | L-valine | 0.65 | 0.65 | | 0.65 | 0.65 | 0.80 | | 0.65 | 0.80 |
| | L-isoleucine | 0.40 | 0.40 | | 0.40 | 0.40 | 0.50 | | 0.40 | 0.50 |
| | L-phenylalanine | 0.15 | 0.15 | | 0.15 | 0.15 | 0.20 | | 0.15 | 0.20 |
| Component E | Sodium DL-lactate | 12.00 | 7.50 | 6.20 | 5.00 | 7.50 | 10.00 | 12.00 | 11.50 | 10.00 |
| | DL-lactic acid | | 3.50 | 5.80 | 5.76 | 4.50 | 2.00 | | | 2.00 |
| Component F | Water | 50.35 | 50.35 | 49.97 | 50.59 | 50.08 | 48.73 | 48.91 | 50.32 | 48.18 |
| Others | Betaine | | | | | | | | | |
| | Sorbitol solution (70%) | | | | | | | | | |
| Preservative | Methylparaben | | | | | | | | | |
| | Propylparaben | | | | | | | | | |
| | Phenoxethanol | | | | | | | | | |
| | Total | 100.00 | 100.00 | 100.00 | 100.00 | 100.00 | 100.00 | 100.00 | 100.00 | 100.00 |

Results for Examples 1-9.

| | | Example 1 | Example 2 | Example 3 | Example 4 | Example 5 | Example 6 | Example 7 | Example 8 | Example 9 |
|---|---|---|---|---|---|---|---|---|---|---|
| pH | | 5.00 | 5.10 | 4.63 | 4.65 | 4.47 | 4.78 | 5.11 | 5.45 | 4.52 |
| Preservative effect | Escherichia coli | ○○ | ○○ | ○○ | ○○ | ○○ | ○○ | ○○ | ○○ | ○○ |
| | Pseudomonas aeruginosa | ○○ | ○○ | ○○ | ○○ | ○○ | ○○ | ○○ | ○○ | ○○ |
| | Staphylococcus aureus | ○○ | ○ | ○○ | ○○ | ○○ | ○○ | ○○ | ○ | ○○ |
| | Candida albicans | ○○ | ○○ | ○○ | ○○ | ○○ | ○○ | ○○ | ○○ | ○○ |
| | Aspergillus niger | ○○ | ○○ | ○○ | ○○ | ○○ | ○○ | ○○ | ○○ | ○○ |
| Low-temperature stability | | ○○ | ○○ | ○ | ○ | Δ | ○○ | ○○ | ○○ | Δ |
| Moisturizing effect | | ○○ | ○○ | ○○ | ○○ | ○○ | ○○ | ○○ | ○○ | ○○ |
| Sticky feeling | | ○○ | ○○ | ○○ | ○○ | ○○ | ○○ | ○○ | ○○ | ○○ |
| Effect of preventing color fading | | ○○ | ○ | ○○ | ○○ | ○○ | ○○ | ○ | ○ | ○○ |
| Component A | | 19.00 | 20.00 | 20.00 | 20.00 | 19.27 | 19.27 | 19.27 | 19.53 | 19.27 |
| Component B | | 8.15 | 8.15 | 6.35 | 8.15 | 8.15 | 8.20 | 8.00 | 8.15 | 8.20 |
| Component C | | 5.20 | 5.20 | 4.88 | 5.20 | 5.20 | 5.20 | 5.20 | 5.20 | 5.75 |
| Component D | | 5.30 | 5.30 | 6.80 | 5.30 | 5.30 | 6.60 | 6.62 | 5.30 | 6.60 |
| Component E | | 12.00 | 11.00 | 12.00 | 10.76 | 12.00 | 12.00 | 12.00 | 11.50 | 12.00 |
| Component F | | 50.35 | 50.35 | 49.97 | 50.59 | 50.08 | 48.73 | 48.91 | 50.32 | 48.18 |
| (Components A + B + C + D + E)/ (Components A + B + C + D + E + F) | | 49.65 | 49.65 | 50.03 | 49.41 | 49.92 | 51.27 | 51.09 | 49.68 | 51.82 |
| (Components A + B + C + D)/ (Components A + B + C + D + E + F) | | 37.65 | 38.65 | 38.03 | 38.65 | 37.92 | 39.27 | 39.09 | 38.18 | 39.82 |
| (Components A + E)/ (Components A + B + C + D + E + F) | | 31.00 | 31.00 | 32.00 | 30.76 | 31.27 | 31.27 | 31.27 | 31.03 | 31.27 |
| (Component A)/ (Components A + E) | | 61.29 | 64.52 | 62.50 | 65.02 | 61.62 | 61.62 | 61.62 | 62.94 | 61.62 |
| (Component A)/ | | 38.27 | 40.28 | 39.98 | 40.48 | 38.60 | 37.59 | 37.72 | 39.31 | 37.19 |

TABLE 2-continued

| | | | | | | | | | |
|---|---|---|---|---|---|---|---|---|---|
| (Components A + B + C + D + E) | | | | | | | | | |
| (Component B)/ | | 16.41 | 16.41 | 12.69 | 16.49 | 16.33 | 15.99 | 15.66 | 16.40 | 15.82 |
| (Components A + B + C + D + E) | | | | | | | | | |
| (Component C)/ | | 10.47 | 10.47 | 9.75 | 10.52 | 10.42 | 10.14 | 10.18 | 10.47 | 11.10 |
| (Components A + B + C + D + E) | | | | | | | | | |
| (Component D)/ | | 10.67 | 10.67 | 13.59 | 10.73 | 10.62 | 12.87 | 12.96 | 10.67 | 12.74 |
| (Components A + B + C + D + E) | | | | | | | | | |
| (Component E)/ | | 24.17 | 22.16 | 23.99 | 21.78 | 24.04 | 23.41 | 23.49 | 23.15 | 23.16 |
| (Components A + B + C + D + E) | | | | | | | | | |

Comparative Examples 1-8.

| | | Comparative Example 1 | Comparative Example 2 | Comparative Example 3 | Comparative Example 4 | Comparative Example 5 | Comparative Example 6 | Comparative Example 7 | Comparative Example 8 |
|---|---|---|---|---|---|---|---|---|---|
| Component A | Sodium L-pyrrolidone carboxylate | | 10.000 | | | 18.00 | 25.00 | 24.00 | |
| | Sodium DL-pyrrolidone carboxylate | 10.00 | | 5.00 | 10.00 | | | | |
| | L-pyrrolidone carboxylic acid | | | 4.30 | | 1.71 | | 4.30 | |
| Component B | L-arginine | 0.30 | 0.30 | 0.30 | 8.00 | 8.00 | 8.00 | 8.00 | 8.00 |
| | L-lysine | 0.35 | 0.35 | 0.35 | | | | | |
| | L-histidine | | | | 0.15 | 0.15 | 0.20 | | |
| Component C | L-glutamic acid | 0.75 | 0.75 | 0.75 | 0.75 | 5.20 | | 0.75 | 0.75 |
| | L-aspartic acid | | | | | | 8.00 | | |
| Component D | Glycine | 1.00 | 1.00 | 1.00 | 1.30 | 1.30 | 1.60 | 1.60 | 1.60 |
| | L-alanine | 0.40 | 0.40 | 0.40 | 1.20 | 1.20 | 1.50 | 3.00 | 3.00 |
| | L-proline | 0.10 | 0.10 | 0.10 | 0.40 | 0.40 | 0.50 | 0.50 | 0.50 |
| | L-serine | 1.50 | 1.50 | 1.50 | 0.80 | 0.80 | 1.00 | 1.02 | 1.02 |
| | L-threonine | 0.20 | 0.20 | 0.20 | 0.40 | 0.40 | 0.50 | 0.50 | 0.50 |
| | L-valine | | | | 0.65 | 0.65 | 0.80 | | |
| | L-isoleucine | | | | 0.40 | 0.40 | 0.50 | | |
| | L-phenylalanine | | | | 0.15 | 0.15 | 0.20 | | |
| Component E | Sodium DL-lactate | | | | 2.10 | 11.50 | 8.00 | | 24.00 |
| | DL-lactic acid | | | 5.40 | 1.52 | | | | 4.30 |
| Component F | Water | 49.20 | 50.90 | 50.70 | 57.18 | 50.14 | 44.20 | 26.33 | 26.33 |
| Others | Betaine | 30.00 | 30.00 | 30.00 | 15.00 | | | 30.00 | 30.00 |
| | Sorbitol solution (70%) | 6.00 | 4.20 | | | | | | |
| Preservative | Methylparaben | 0.20 | | | | | | | |
| | Propylparaben | 0.005 | | | | | | | |
| | Phenoxyethanol | | 0.30 | | | | | | |
| | Total | 100.00 | 100.00 | 100.00 | 100.00 | 100.00 | 100.00 | 100.00 | 100.00 |

Results for Comparative Examples 1-8.

| | | Comparative Example 1 | Comparative Example 2 | Comparative Example 3 | Comparative Example 4 | Comparative Example 5 | Comparative Example 6 | Comparative Example 7 | Comparative Example 8 |
|---|---|---|---|---|---|---|---|---|---|
| pH | | 5.52 | 6.52 | 4.50 | 5.28 | 5.80 | 6.28 | 5.00 | 5.00 |
| Preservative effect | Escherichia coli | X | ○○ | ○○ | ○○ | ○○ | X | X | ○ |
| | Pseudomonas aeruginosa | ○ | ○○ | ○○ | ○○ | ○○ | ○○ | ○○ | ○○ |
| | Staphylococcus aureus | X | ○○ | ○ | ○○ | X | X | X | ○ |
| | Candida albicans | ○ | ○○ | ○○ | ○○ | X | ○○ | ○○ | ○○ |
| | Aspergillus niger | ○ | X | X | X | ○ | X | X | X |
| Low-temperature stability | | ○○ | ○○ | Δ | ○○ | ○○ | ○○ | ○○ | ○○ |
| Moisturizing effect | | ○ | ○ | Δ | Δ | ○○ | ○○ | ○ | Δ |
| Sticky feeling | | ○○ | ○○ | Δ | ○○ | ○○ | ○○ | ○ | ○○ |
| Effect of preventing color fading | | Δ | Δ | X | Δ | ○ | Δ | ○○ | X |
| Component A | | 10.00 | 10.00 | 9.30 | 10.00 | 19.71 | 25.00 | 28.30 | 0.00 |
| Component B | | 0.65 | 0.65 | 0.65 | 8.15 | 8.15 | 8.20 | 8.00 | 8.00 |
| Component C | | 0.75 | 0.75 | 0.75 | 0.75 | 5.20 | 8.00 | 0.75 | 0.75 |
| Component D | | 3.20 | 3.20 | 3.20 | 5.30 | 5.30 | 6.60 | 6.62 | 6.62 |
| Component E | | 0.00 | 0.00 | 5.40 | 3.62 | 11.50 | 8.00 | 0.00 | 28.30 |
| Component F | | 49.20 | 50.90 | 50.70 | 57.18 | 50.14 | 44.20 | 26.33 | 26.33 |
| (Components A + B + C + D + E)/ (Components A + B + C + D + E + F) | | 22.89 | 22.29 | 27.57 | 32.73 | 49.86 | 55.80 | 62.39 | 62.39 |
| (Components A + B + C + D)/ (Components A + B + C + D + E + F) | | 22.89 | 22.29 | 19.86 | 28.47 | 38.36 | 47.80 | 62.39 | 21.96 |
| (Components A + E)/ (Components A + B + C + D + E + F) | | 15.68 | 15.27 | 21.00 | 16.02 | 31.21 | 33.00 | 40.43 | 40.43 |
| (Component A)/ (Components A + E) | | 100.00 | 100.00 | 63.27 | 73.42 | 63.15 | 75.76 | 100.00 | 0.00 |
| (Component A)/ (Components A + B + C + D + E) | | 68.49 | 68.49 | 48.19 | 35.94 | 39.53 | 44.80 | 64.80 | 0.00 |
| (Component B)/ (Components A + B + C + D + E) | | 4.45 | 4.45 | 3.37 | 29.29 | 16.35 | 14.70 | 18.32 | 18.32 |
| (Component C)/ | | 5.14 | 5.14 | 3.89 | 2.70 | 10.43 | 14.34 | 1.72 | 1.72 |

TABLE 2-continued

| | | | | | | | | |
|---|---|---|---|---|---|---|---|---|
| (Components A + B + C + D + E (ComponentD)/ (Components A + B + C + D + E) | 21.92 | 21.92 | 16.58 | 19.05 | 10.63 | 11.83 | 15.16 | 15.16 |
| (Component E)/ (Components A + B + C + D + E) | 0.00 | 0.00 | 27.98 | 13.02 | 23.06 | 14.34 | 0.00 | 64.80 |

In Table 2, Examples 1 to 9 in which the respective components were incorporated at a specific ratio and at a specific pH exhibited an extremely high preservative effect on all the species of microorganisms. Further, they were also excellent in low-temperature stability, a moisturizing property, stickiness, and an effect of preventing color fading. Example 5 in which the pH was particularly low, being 4.5 or lower, and Example 9 in which glutamic acid was used as (Component C) had a tendency that the low-temperature stability was a little poor. However, the other Examples exhibited an excellent low-temperature stability. On the other hand, in Comparative Examples 1 and 2, although a preservative which is commonly used for cosmetic purpose was incorporated in an amount commonly used, the preservative effect on some microorganisms, particularly on *Aspergillus niger* was not sufficient. Further, although the moisturizing property and less-stickiness were good, the effect of preventing dyed hair from color fading was not sufficient.

In Comparative Example 3 and Comparative Example 4, although the pH of the formulations fell within the range of the invention, [the total weight of (Component A)+(Component E)], and the weight of (Component C)/[the total weight of (Component A)+(Component B)+(Component C)+(Component D)+(Component E)] were lacking, and the preservative effect on *Aspergillus niger* and the moisturizing effect were not sufficient.

In Comparative Example 5 and Comparative Example 6, the pH of the formulations was higher than 5.5, and the preservative effect on several strains of microorganisms was not sufficient. In Comparative Examples 7 and 8, in which (Component A) and (Component E) were incorporated alone, respectively, the preservative effect mainly on *Aspergillus niger* was not sufficient, and moreover, there was a tendency that the moisturizing effect was also lowered.

Formulation Example 1

A hair shampoo formulation with a composition shown in the following Table 3 was prepared.

TABLE 3

| | (% by weight) |
|---|---|
| Sodium cocoyl alanine (30%) | 22.0 |
| Lauramidopropyl hydroxysultaine (30%) | 18.0 |
| Sodium olefin (C14-16) sulfonate | 3.0 |
| Cocamide MEA | 1.0 |
| Polyquaternium-7 (8%) | 5.0 |
| Aqueous preservative solution with a high amino acid content (Example 1) | 5.0 |
| Glycol distearate | 1.0 |
| Methylparaben | 0.2 |
| Perfume | 0.5 |
| Citric acid monohydrate (20%) | 1.8 |
| Water | 42.5 |
| | 100.0 |

INDUSTRIAL APPLICABILITY

By incorporating lactic acid and/or a salt thereof (Component E) and water (Component F) in an aqueous solution containing a high content of pyrrolidone carboxylic acid and/or a salt thereof (Component A), a basic amino acid and/or a salt thereof (Component B), an acidic amino acid and/or a salt thereof (Component C) and a neutral amino acid and/or a salt thereof (Component D) at a specific incorporation ratio and at a specific pH, it has become possible to provide an aqueous preservative solution with a high amino acid content which is excellent in preservation, particularly a preservative effect on fungi, and safety, and is excellent in storage stability so as not to cause a problem such as depositing, coloring or smelling even when it is stored for a long time, and when incorporated in a cosmetic, is capable of imparting a high moisturizing effect without causing a sticky feeling, and imparting an effect of preventing dyed hair from color fading. Further, it is significant that a variety of cosmetics which are free from a sticky feeling while imparting a high moisturizing effect and have an effect of preventing dyed hair from color fading can be provided by incorporating this solution therein.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. An aqueous preservative solution with a high amino acid content, comprising:
   (A) at least pyrrolidone carboxylic acid and/or a salt thereof;
   (B) at least one basic amino acid and/or a salt thereof;
   (C) at least one acidic amino acid and/or a salt thereof
   (D) at least one neutral amino acid and/or a salt thereof;
   (E) lactic acid and/or a salt thereof; and
   (F) water,
   wherein:
   component (A) and component (E) are present in a total amount of from 25 to 40% by weight, based on the total weight of component (A), component (B), component (C), component (D), component (E), and component (F),
   component (A) is present in an amount of from 50 to 95% by weight, based on the total weight of component (A) and component (E),
   component (A), component (B), component (C), and component (D) are present in a total amount of from 23 to 60% by weight, based on the total weight of component (A), component (B), component (C), component (D), component (E), and component (F), and
   the pH of the solution is from 3.5 to 5.5.

2. An aqueous preservative solution with a high amino acid content according to claim 1,
wherein:
component (A), component (B), component (C), and component (D) are present in a total amount of from 28 to 60% by weight, based on the total weight of component (A), component (B), component (C), component (D), component (E), and component (F).

3. An aqueous preservative solution with a high amino acid content according to claim 1,
wherein:
component (A), component (B), component (C), and component (D) are present in a total amount of from 30 to 60% by weight, based on the total weight of component (A), component (B), component (C), component (D), component (E), and component (F).

4. An aqueous preservative solution with a high amino acid content according to claim 1,
wherein:
component (B) is arginine and/or a salt thereof, and
component (B) is present in an amount of from 4 to 25% by weight, based on the total weight of component (A), component (B), component (C), component (D), and component (E).

5. An aqueous preservative solution with a high amino acid content according to either claim 1,
wherein:
component (C) is aspartic acid and/or a salt thereof, and
component (C) is present in an amount of from 5 to 15% by weight, based on the total weight of component (A), component (B), component (C), component (D), and component (E).

6. An aqueous preservative solution with a high amino acid content according to either claim 4,
wherein:
component (C) is aspartic acid and/or a salt thereof, and
component (C) is present in an amount of from 5 to 15% by weight, based on the total weight of component (A), component (B), component (C), component (D), and component (E).

7. An aqueous preservative solution with a high amino acid content according to claim 1,
wherein:
component (D) is one or more members selected from the group consisting of glycine, a salt of glycine, alanine, a salt of alanine, an mixtures thereof, and
component (D) is present in an amount of from 5 to 20% by weight, based on the total weight of component (A), component (B), component (C), component (D), component (E).

8. An aqueous preservative solution with a high amino acid content according to claim 4,
wherein:
component (D) is one or more members selected from the group consisting of glycine, a salt of glycine, alanine, a salt of alanine, an mixtures thereof, and
component (D) is present in an amount of from 5 to 20% by weight, based on the total weight of component (A), component (B), component (C), component (D), component (E).

9. An aqueous preservative solution with a high amino acid content according to claim 5,
wherein:
component (D) is one or more members selected from the group consisting of glycine, a salt of glycine, alanine, a salt of alanine, an mixtures thereof, and
component (D) is present in an amount of from 5 to 20% by weight, based on the total weight of component (A), component (B), component (C), component (D), component (E).

10. An aqueous preservative solution with a high amino acid content according to claim 4,
wherein:
component (A), component (B), component (C), and component (D) are present in a total amount of from 28 to 60% by weight, based on the total weight of component (A), component (B), component (C), component (D), component (E), and component (F).

11. An aqueous preservative solution with a high amino acid content according to claim 5,
wherein:
component (A), component (B), component (C), and component (D) are present in a total amount of from 28 to 55% by weight, based on the total weight of component (A), component (B), component (C), component (D), component (E), and component (F).

12. An aqueous preservative solution with a high amino acid content according to claim 7,
wherein:
component (A), component (B), component (C), and component (D) are present in a total amount of from 28 to 60% by weight, based on the total weight of component (A), component (B), component (C), component (D), component (E), and component (F).

13. An aqueous preservative solution with a high amino acid content according to claim 4,
wherein:
component (A), component (B), component (C), and component (D) are present in a total amount of from 30 to 60% by weight, based on the total weight of component (A), component (B), component (C), component (D), component (E), and component (F).

14. An aqueous preservative solution with a high amino acid content according to claim 5,
wherein:
component (A), component (B), component (C), and component (D) are present in a total amount of from 30 to 60% by weight, based on the total weight of component (A), component (B), component (C), component (D), component (E), and component (F).

15. An aqueous preservative solution with a high amino acid content according to claim 7,
wherein:
component (A), component (B), component (C), and component (D) are present in a total amount of from 30 to 60% by weight, based on the total weight of component (A), component (B), component (C), component (D), component (E), and component (F).

16. A cosmetic, comprising an aqueous preservative solution with a high amino acid content according to claim 1.

17. A cosmetic, comprising an aqueous preservative solution with a high amino acid content according to claim 4.

18. A cosmetic, comprising an aqueous preservative solution with a high amino acid content according to claim 5.

19. A cosmetic, comprising an aqueous preservative solution with a high amino acid content according to claim 7.

20. A cosmetic, comprising an aqueous preservative solution with a high amino acid content according to claim 2.

21. An aqueous preservative solution with a high amino acid content according to claim 1, wherein:
component (A) is present in an amount of from 52 to 95% by weight, based on the total weight of component (A) and component (E).

22. An aqueous preservative solution with a high amino acid content according to claim 1,
wherein:
component (A) is present in an amount of from 54 to 95% by weight, based on the total weight of component (A) and component (E).

23. An aqueous preservative solution with a high amino acid content according to claim 1,
wherein:
component (A) is present in an amount of from 56 to 95% by weight, based on the total weight of component (A) and component (E).

24. An aqueous preservative solution with a high amino acid content according to claim 1,
wherein:
component (A) is present in an amount of from 60 to 95% by weight, based on the total weight of component (A) and component (E).

25. An aqueous preservative solution with a high amino acid content according to claim 1,
wherein:
component (A) is present in an amount of from 52 to 90% by weight, based on the total weight of component (A) and component (E).

26. An aqueous preservative solution with a high amino acid content according to claim 1,
wherein:
component (A) is present in an amount of from 54 to 90% by weight, based on the total weight of component (A) and component (E).

27. An aqueous preservative solution with a high amino acid content according to claim 1,
wherein:
component (A) is present in an amount of from 56 to 90% by weight, based on the total weight of component (A) and component (E).

28. An aqueous preservative solution with a high amino acid content according to claim 1,
wherein:
component (A) is present in an amount of from 60 to 90% by weight, based on the total weight of component (A) and component (E).

* * * * *